US00PP34034P2

(12) United States Plant Patent
Bak et al.

(10) Patent No.: US PP34,034 P2
(45) Date of Patent: Mar. 15, 2022

(54) ***TILLANDSIA* PLANT NAMED 'DOLCE'**

(50) Latin Name: ***Tillandsia* hybrid**
Varietal Denomination: DOLCE

(71) Applicant: Corn Bak B.V., Assendelft (NL)

(72) Inventors: Elly Bak, Rijsenhout (NL); Nicolaas D. M. Steur, Oude Niedorp (NL)

( * ) Notice: Subject to any disclaimer, the term of this patent is extended or adjusted under 35 U.S.C. 154(b) by 0 days.

(21) Appl. No.: 17/470,377

(22) Filed: Sep. 9, 2021

(51) Int. Cl.
*A01H 5/02* (2018.01)
*A01H 6/22* (2018.01)

(52) U.S. Cl.
USPC ..... Plt./370
CPC ..... *A01H 6/22* (2018.05)

(58) Field of Classification Search
USPC ..... Plt./370
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Tillandsia* plant named 'DOLCE' is disclosed, characterized by solid growth habit, funnel-form rosette plant, measuring about 40 cm in height (above the pot when flowering); numerous green colored foliage, measuring about 50 cm in length and about 5 cm in width; abundant floral bract production; bracts have unique red-purple inflorescence; panicle inflorescence, measuring about 45 cm in height (flowering part) and about 28 cm in diameter; and log-lasting habit. The new variety is a *Tillandsia*, typically produced as an ornamental plant.

1 Drawing Sheet

Latin name of the genus and species: *Tillandsia* hybrid.
Variety denomination: 'DOLCE'.

BACKGROUND OF THE INVENTION

The present invention relates to a new and distinct cultivar of *Tillandsia* plant, botanically known as *Tillandsia* hybrid, of the family Bromeliaceae, and hereafter referred to as 'DOLCE'.

The new *Tillandsia* 'Dolce' originated from a cross made in a controlled breeding program by the inventors in 2003. The seed parent is the unnamed and unpatented *Tillandsia* selection identified by code '0307140001'. The pollen parent is the unnamed and unpatented *Tillandsia* selection identified by code '0307140004'. The new *Tillandsia* was discovered and selected by the inventors in 2008 as a single flowering plant within the progeny of the stated cross in a controlled environment in Assendelft, the Netherlands.

Asexual reproduction of the new cultivar 'DOLCE' was first performed by off-shoots beginning in 2015, and then by tissue culture beginning in 2017 in Assendelft, the Netherlands. The new cultivar reproduces true to type.

Methods for cultivation and crossing of *Tillandsia* are well known. For a detailed discussion, reference is made to the following publications, which are incorporated herein by reference: Benzig, David H., THE BIOLOGY OF THE BROMELIADS, Mad River Press, Inc., Eureka (1980); Zimmer, Karl, BROMELEIN, Verlag, Paul Parey, Berlin (1986); and Rauh, Werner, BROMELEIN, Verlag Eugen Ulmer, Stuttgart (1981).

SUMMARY OF THE INVENTION

The following traits have been repeatedly observed and are determined to be the unique characteristics of 'DOLCE', which in combination distinguish 'DOLCE' as a new and distinct *Tillandsia* cultivar:

1. Solid growth habit; upright and not lodging over.
2. Funnel-form rosette plant, measuring about 40 cm in height (above the pot when flowering).
3. Numerous, green colored foliage, measuring about 50 cm in length and 5 cm in width.
4. Erect panicle with side branches, red-purple inflorescence.
5. Long-lasting as a consumer product.

PARENT COMPARISONS

Plants of the parent cultivars are no longer available to provide a botanical comparison with the new *Tillandsia* hybrid 'DOLCE'.

COMMERCIAL COMPARISONS

Plants of *Tillandsia* 'DOLCE' are similar in some horticultural characteristics to the variety *Tillandsia* 'Samantha', unpatented. The new variety, however, differs in the following:

1. The new variety has a red-purple inflorescence, while this comparator has a red-purple with green inflorescence.

BRIEF DESCRIPTION OF THE PHOTOGRAPH

The accompanying photograph illustrates the overall appearance of the new *Tillandsia* cultivar 'DOLCE' showing the colors as true as is reasonably possible with colored reproductions of this type. Colors in the photograph may differ slightly from the color values cited in the detailed botanical description which accurately describes the color of 'DOLCE'. The accompanying figure shows a side perspective view of a typical potted flowering plant of 'DOLCE' at about 16 months of age from potting.

DETAILED BOTANICAL DESCRIPTION

'DOLCE' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant. For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant.

The aforementioned photograph, together with the following observations, measurements and values describe the new *Tillandsia* 'DOLCE' as grown in a greenhouse in Assendelft, The Netherlands, under conditions which closely approximate those generally used in commercial practice. Plants of 'DOLCE' were grown in a greenhouse with day temperatures ranging from 20° C. to 28° C. and night temperatures ranging from 18° C. to 23° C. No artificial lighting or photoperiodic treatments were conducted, but plants of 'DOLCE' are forced into flowering. The following fertilizer is added when growing plants of 'DOLCE': 1 part nitrogen, 0.6 parts phosphor, 2 parts Kalium and 0.1 parts magnesium.

Color references are made to The Royal Horticultural Society Colour Chart (R.H.S.), 2001 edition, except where general colors of ordinary significance are used. Color values were taken under daylight conditions in a greenhouse in Assendelft, The Netherlands. The age of the plants of 'DOLCE' described is about 18 weeks after flowering treatment.

Botanical classification: *Tillandsia* hybrid 'DOLCE'.

PROPAGATION

Propagation method: Tissue culture.

PLANT

General appearance and form:
- *Shape*.—Funnel-form rosette.
- *Height*.—About 40 cm when flowering.
- *Width*.—About 65 cm.

Growth habit: Outwardly arching rotate foliage surrounding an upright inflorescence.

Plant vigor: Good.

Flowering season: A fully grown plant can flower year-round, starting about 18 weeks after induction of natural light or through flowering treatment.

Cold tolerance: Frost tender. Temperatures below 5° C. may damage plants.

Fragrance: None.

FOLIAGE

Leaf:
- *Quantity*.—About 18, depending on the size of the plant.
- *Average length*.—50 cm when flowering.
- *Average width*.—5 cm.
- *Shape*.—Linear.
- *Apex*.—Acuminate.
- *Base*.—Strap-like around central axis.
- *Margin*.—Entire.
- *Texture*.—Smooth, both sides.
- *Orientation*.—Leaf blades arch continuously from base.
- *Color* (*varies somewhat depending on growing conditions*).—Mature and Immature, Upper Side: RHS Green 137B. Mature and Immature, Under Side: RHS Green 137B to 144A.

INFLORESCENCE

Flowers are mostly disposed within the floral bracts and rarely open full.
- *Borne*.—Erect stalks.
- *Type*.—Panicle.
- *Length*.—About 88 cm, flowering part 45 cm.
- *Diameter*.—About 28 cm.
- *Flowers per inflorescence*.—Average 115.
- *Color*.—Near RHS Red-Purple 58C.

Petals:
- *Quantity*.—3 per flower.
- *Length*.—About 4.5 cm.
- *Width*.—About 0.5 cm.
- *Shape*.—Ligulate.
- *Apex*.—Obtuse.
- *Base*.—Fused.
- *Color*.—Upper Surface: Near RHS Violet-Blue 93A. Under Surface: Near RHS Violet-Blue 93A.

Sepals:
- *Quantity*.—3 per flower.
- *Length*.—About 3.5 cm.
- *Width*.—About 0.8 cm.
- *Shape*.—Ligulate.
- *Apex*.—Acute.
- *Base*.—Fused.
- *Color*.—Near RHS White 155A, apex near Red-Purple 63B.

Scape:
- *Number*.—1.
- *Length*.—About 80 cm.
- *Width*.—About 2 cm.
- *Scape bracts*.—Quantity: About 12. Arrangement: Alternate. Length: Average 20 cm. Width: 4 to 5 cm. Shape: Linear. Apex: Acuminate. Base: Fused. Margin: Entire. Texture: Smooth. Color, Upper and Under Surfaces: Near RHS Yellow-Green 144B.

Primary bracts:
- *Quantity*.—About 12.
- *Arrangement*.—Alternate.
- *Length*.—7 to 15 cm.
- *Width*.—About 2 cm.
- *Shape*.—Lanceolate, tips curved downwards.
- *Apex*.—Acute.
- *Base*.—Fused.
- *Margin*.—Entire.
- *Texture*.—Smooth.
- *Color, upper and under surfaces*.—Near RHS Red-Purple 58C.

Branches:
- *Quantity*.—About 10.
- *Length*.—About 16 cm.
- *Diameter*.—About 2.5 cm.
- *Color, upper and under surfaces*.—Near RHS Red-Purple 58C.

Floral bracts:

*Quantity*.—About 115.

*Length*.—About 4 cm.

*Diameter*.—About 2 cm.

*Shape*.—Lanceolate.

*Apex*.—Acute.

*Base*.—Fused.

*Margin*.—Entire.

*Texture*.—Smooth.

*Color, upper and under surfaces*.—Near RHS Red-Purple 58C.

REPRODUCTIVE ORGANS

Androecium:

*Stamen*.—Number: 6 per flower. Length: About 2.5 cm. Diameter: About 0.1 mm. Color: Near RHS White 155D.

*Anther*.—Length: About 0.5 cm. Color: Near RHS Yellow 13A. Pollen: None.

Gynoecium:

*Stigma*.—Shape: 3-parted. Width: About 0.2 cm. Color: Near RHS Brown 200C.

*Style*.—Length: About 3.7 cm. Color: Near RHS Yellow-White 158B to Brown 200C.

*Ovary*.—Position: Superior. Shape: Conical. Length: About 1.8 cm. Diameter: About 0.4 cm.

OTHER CHARACTERISTICS

Seeds: Not observed.

Fruit: Not observed.

Disease/pest resistance: No resistance nor susceptibility to normal diseases and pests of *Tillandsia* have been observed.

What is claimed is:

1. A new and distinct cultivar of *Tillandsia* plant named 'DOLCE' as herein illustrated and described.

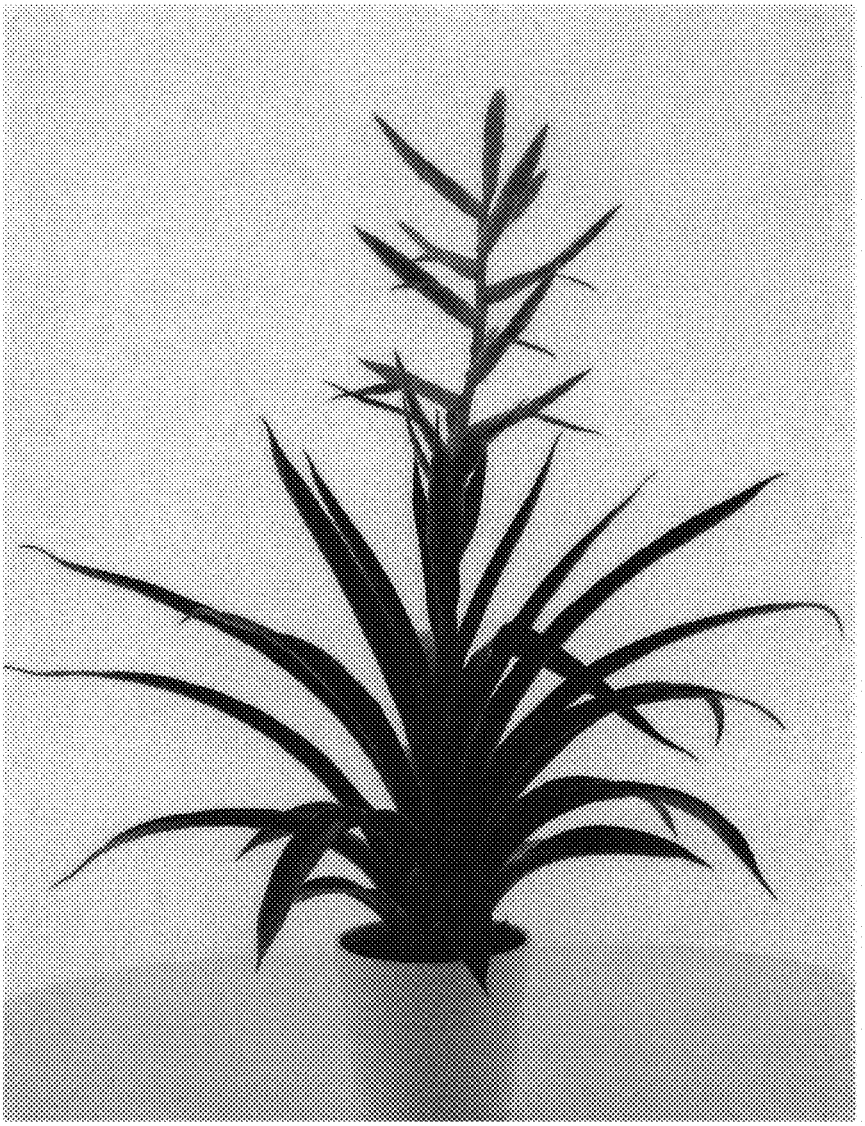

* * * * *